United States Patent [19]

Yin

[11] Patent Number: 4,521,688
[45] Date of Patent: Jun. 4, 1985

[54] THREE-DIMENSIONAL AND TOMOGRAPHIC IMAGING DEVICE FOR X-RAY AND GAMMA-RAY EMITTING OBJECTS

[75] Inventor: Lo I. Yin, Silver Spring, Md.

[73] Assignee: The United States of America as represented by the Administrator of the National Aeronautics and Space Administration, Washington, D.C.

[21] Appl. No.: 459,842

[22] Filed: Jan. 21, 1983

[51] Int. Cl.³ .................................................. G01T 1/16
[52] U.S. Cl. ................................... 250/363 S; 250/369
[58] Field of Search .................. 378/2; 250/363 S, 369

[56] References Cited

U.S. PATENT DOCUMENTS

| | | | |
|---|---|---|---|
| 3,452,657 | 7/1969 | Cox | 354/202 |
| 3,503,315 | 3/1970 | de Montebello | 354/112 |
| 3,535,993 | 10/1970 | Jones | 354/112 |
| 3,613,539 | 10/1971 | Dudley | 354/354 |
| 4,142,101 | 2/1979 | Yin | 250/363 R |
| 4,345,153 | 8/1982 | Yin | 250/369 |
| 4,404,469 | 9/1983 | Yin | 250/363 R |
| 4,424,446 | 1/1984 | Inbar et al. | 250/363 S |

OTHER PUBLICATIONS

Three-Dimensional Imaging of X-Ray and Gamma-Ray Objects in Real Time, Yin et al., Applied Optics, vol. 19, No. 17, Sep. 1, 1980.
On the Multiplex Advantage of Coded Source/Aperture Photon Imaging, Wagner et al., Society of Photo-optical Instrumentation Engineers, (SPIE), vol. 314, (Conference on Digital Radiography), p. 72, 1981.
Wide-angle Integral Photography-The Integram System, R. L. de Montebello, SPIE, vol. 120, Three Dimensional Imaging, (1977).

*Primary Examiner*—Bruce C. Anderson
*Assistant Examiner*—Constantine Hannaher
*Attorney, Agent, or Firm*—John O. Tresansky; John R. Manning; Ronald F. Sandler

[57] ABSTRACT

An instrument for obtaining quantitative, three-dimensional and tomographic information relating to x-ray and gamma-ray emitting objects and for the orthoscopic viewing of such objects includes a multiple-pinhole aperture plate (22) held spaced from an x-ray or gamma-ray to visible-light converter (24) which is coupled to a visible-light image intensifier (26). The spacing between the aperture plate and the converter is chosen such that the mini-images of an emitting object formed by the pinholes do not substantially overlap as they impinge on the converter. The output of the image intensifier is digitized by a digitizing camera (36) in terms of position and intensity and fed into a digital computer (40,42). The computer may output quantitative information relating to the emitting object directly, such as that relating to tomograms, or provide information in analogue form when coupled with a suitable viewing device (52,54), to give an orthoscopic, three-dimensional image of the object.

62 Claims, 3 Drawing Figures

THREE-DIMENSIONAL AND TOMOGRAPHIC IMAGING DEVICE FOR X-RAY AND GAMMA-RAY EMITTING OBJECTS

ORIGIN OF THE INVENTION

The invention described herein was made by an employee of the United States Government and may be manufactured and used by or for the Government for governmental purposes without the payment of any royalties thereon or therefor.

1. Technical Field

This invention pertains to invisible radiant energy imaging and, more particularly, to the conversion of x-rays and gamma rays emitted by an object into a visible auto-stereoscopic image or qualitative or quantitative tomographic information.

2. Background Art

The contributions of modern physics have increased the availability of radioactive x-ray and gamma-ray emitting materials in industry and nuclear medicine. As radioactive emission principally occurs outside of the visible part of the electromagnetic spectrum, an unaided human observer is unable to "see" a source of radioactive emission. Various techniques exist to locate a source of radioactive emission. One technique requires a trial and error search with a Geiger counter. Another technique uses a scintillation detector. The information provided by these techniques is limited to the intensity and location of the radioactive emission, and reveals nothing about the shape of a radioactive object or the distribution of radioactivity within the object. An x-ray camera formed by placing an x-ray sensitive film behind a pinhole in an x-ray shield merely provides a recording of a two-dimensional facsimile of an x-ray or gamma-ray emitting object in one perspective. Furthermore, a single pinhole aperture camera is rendered extremely inefficient by the minute aperture of the pinhole.

Other existing x-ray or gamma-ray cameras employ either parallel or converging collimators to bring an essentially parallel beam projection of a radioactive object onto a detector. The detector may be in the nature of a scintillator or a phosphor material which converts x-rays and gamma rays into visible light or it may be a film. Where visible light is generated together with positional information, the visible light is processed by any of a wide variety of methods using such devices as photomultiplier tubes (e.g., Anger cameras), image intensifiers, visible light cameras, video cameras, and centroid-computing electronics in various combinations. Without the additional steps of making successive exposures and subsequent reconstructions, a particular object-to-camera geometry provides only a two-dimensional, single perspective image of an x-ray or gamma-ray emitting object. Although a stereoscopic pair of such cameras may be used to obtain a stereoscopic pair of images which, upon reconstruction, provide a stereoscopic view of a single perspective of an object, that view lacks full horizontal and vertical parallax.

Still other devices employ multiple pinhole arrays or Fresnel zone plates for x-ray or gamma-ray imaging which are generally designated as coded apertures. In such devices, the x-ray image produced by each aperture element overlaps the images produced by the other aperture elements. Because the opposite image produced is not humanly recognizable, a decoding process must be employed to recover the true image of the original object. These devices work adequately for separated point sources but have difficulty in the reconstruction of extended objects because of poor signal-to-background ratios. For the same reason, tomographic images can be obtained only with great difficulty. This makes the three-dimensional reconstruction of the emitting object extremely difficult.

A different approach from that of the coded aperture which has been described as capable of producing three-dimensional and tomographic imaging of x-rays and gamma-ray emitting objects employs sequential pinholes. In this approach, a small array of pinholes, for example, 9, is used in time sequence where only one pinhole is opened at a given time and a separate image is recorded on the same detector for each pinhole.

This procedure avoids confusion as to the contribution of each pinhole at the detector and thereby makes it possible for relatively simple computer-aided reconstruction of the object through back-projection. In contrast to the coded aperture, this sequential pinhole approach results in superior signal-to-background ratios in the reconstructed image. Nevertheless, the sequential pinhole approach has several inherent disadvantages. Because of the sequential operation of the device, the emitting object can not be time varying in either intensity or position. Further, under normal circumstances, the device has a limited number of pinholes because of a desire to limit the time for sequential operation and this limiting of pinholes limits the collection efficiency of the device.

A device has been developed to provide real-time viewing of an x-ray or gamma-ray emitting object in three dimensions with full horizontal and vertical parallax. This has been accomplished by employing a multiple pinhole array, the material of which is impervious to x-rays and gamma rays, placed in front of an x-ray or gamma-ray image intensifier. The pinholes form non-overlapping images of the x-ray or gamma-ray emitting object on the intensifier input. The output of the intensifier can be viewed with a similar pinhole array or a properly designed "fly's eye" lens. This real-time device may produce a pseudoscopic image, i.e., a three-dimensional image with reversed depth, or with the addition of an additional intensifier and pinhole array or lens, it may be made orthoscopic. However, this device requires relatively "hot" radioactive objects because of its relatively low sensitivity. The device is essentially an analogue device incapable of giving quantitative information concerning the radioactive objects and is also incapable, by itself, of creating a permanent record. Furthermore, when a second stage is added to provide an orthoscopic image, image resolution is degraded and additional noise is introduced into the system.

STATEMENT OF THE INVENTION

Accordingly, it is an object of this invention to provide a device giving analogue, visible-light, three-dimensional orthoscopic images of x-ray and gamma-ray emitting objects.

It is another object of the invention to provide a device giving digitally reconstructed, three-dimensional orthoscopic images of x-ray and gamma-ray emitting objects.

It is yet another object of the invention to provide a device giving digitally reconstructed tomograms of x-ray and gamma-ray emitting objects.

It is still another object to provide a device giving three-dimensional images or tomograms of x-ray or gamma-ray emitting objects of low intensity.

It is a further object to provide a device giving three-dimensional images or tomograms for time-varying x-ray or gamma-ray emitting objects.

It is a still further object to provide a device giving a permanent record of quantitative information relating to x-ray or gamma-ray emitting objects.

It is a yet further object to provide a device giving a magnified, true-size, or de-magnified three-dimensional images of x-ray or gamma-ray emitting objects.

It is still another object to provide a device giving three-dimensional images with intentional dimensional exaggerations of x-ray or gamma-ray emitting objects.

Briefly, these and other objects are achieved in one embodiment with a device having a multiple-pinhole aperture plate held spaced apart from an x-ray or gamma-ray imaging detector. The spacing between the aperture plate and the detector is chosen such that the mini-images of an x-ray or gamma-ray emitting object formed by the pinholes do not substantially overlap as they impinge on the detector. The output of the detector is digitized. When the digital signals are fed into a properly programmed digital computer, the computer may output quantitative information relating to an x-ray or gamma-ray emitting object, sensed by the device, in a digital format, or alternatively, provide the same information in analogue form which, when coupled with a suitable viewing device, gives an orthoscopic, three-dimensional image of the object.

DETAILED DESCRIPTION OF THE DRAWINGS

Figure 1:
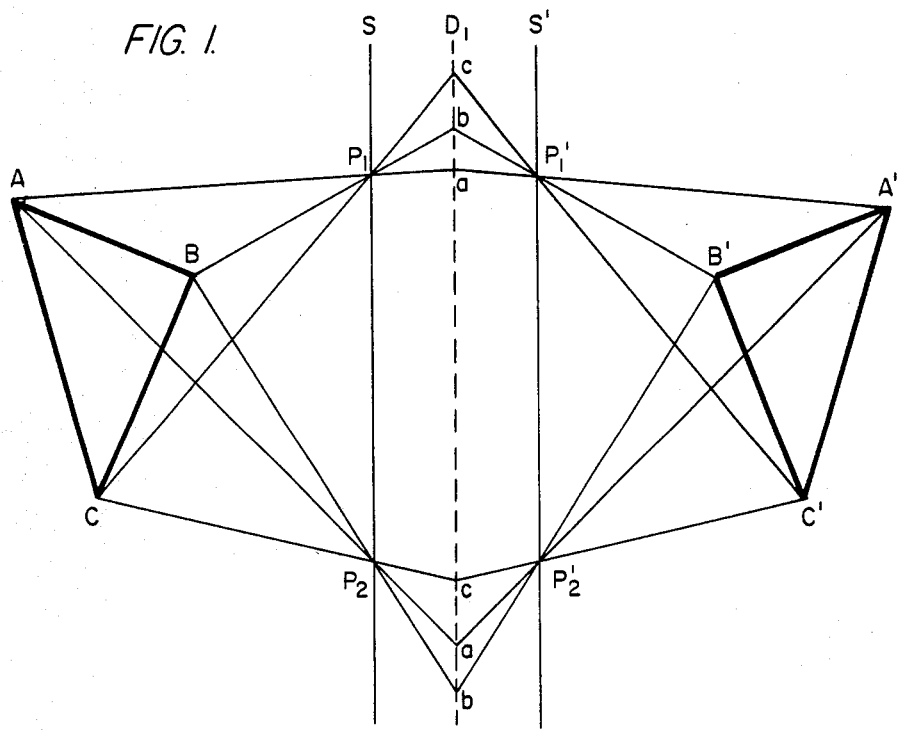
FIG. 1 is a schematic representation of the principle of three-dimensional imaging of an object.

Reference is now made to the drawings and, in particular, to FIG. 1, where a pinhole screen analogy illustrates the principle of three-dimensional imaging used in the present invention. An x-ray or gamma-ray emitting object ABC is situated in front of a screen S containing a multiplicity of pinhole apertures spaced apart in a planar array. Screen S is made of a material otherwise impervious to x-rays and gamma rays. A non-inverting x-ray imaging detector $D_1$ is placed in position with its input surface parallel to and a short distance from the right of screen S, to convert x-ray and gamma-ray images into intensified visible light images at unity magnification. Each pinhole individually operates as a pinhole camera. By using pinholes $P_1$ and $P_2$ as an exemplary pair, two inverted x-ray mini-images abc of object ABC form on the receiving or input surface of detector $D_1$. These mini-images are converted into intensified visible-light images abc at the emitting or output surface of detector $D_1$. The separations between adjacent pinholes $P_1$ and $P_2$ and between S and $D_1$ are chosen so that the mini-images abc do not significantly overlap each other. A second screen, S', may be positioned at the same distance from the output surface of detector $D_1$ as screen S is from the input surface of detector $D_1$, to enable reconstruction of object ABC. Screen S' contains a plurality of pinhole apertures distributed across its surface in a planar array preferably identical to and aligned with the array of pinholes in screen S. Screen S' is made from a material opaque to visible light. When viewed through pinholes $P_1'$ and $P_2'$, spatially corresponding to and aligned with pinholes $P_1$ and $P_2$, the mini-images abc will form a visible light reconstruction A'B'C' of the x-ray or gamma-ray emitting object ABC. The reconstructed image A'B'C' is a real image situated in front of screen S' toward the viewer, with a magnification of unity. Although the image A'B'C' is an upright image, it is pseudoscopic, that is, the depth of the object ABC is reversed when viewed through screen S'. For instance, in FIG. 1 it can be seen that point B' is now away from the viewer rather than toward the viewer as point B is in object ABC. Screen S contains many pinholes like $P_1$ and $P_2$, each having a slightly different perspective view of the object ABC. Therefore, the reconstructed image A'B'C' may be viewed through screen S' over a range of different directions, thereby providing a viewer with both horizontal and vertical parallax. The reconstructed image A'B'C' is, therefore, truly three-dimensional or auto-stereoscopic. This three-dimensional effect is most pronounced when the object viewed fills the field-of-view defined by the distance between the pinholes and the separation between screen S and detector $D_1$. In the configuration shown in FIG. 1, the field-of-view is that field providing the largest mini-images abc possible without overlap occurring between adjacent mini-images.

Figure 2:
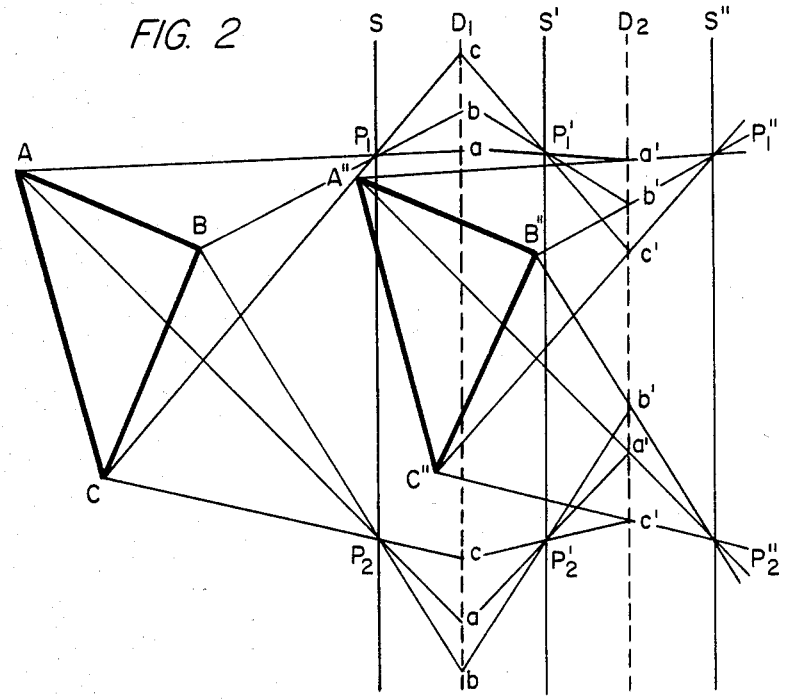
FIG. 2 is a schematic representation of the principle of producing an orthoscopic, three-dimensional image of an object.

Referring now to FIG. 2, a schematic of another pinhole screen analogy shows that an orthoscopic image of an x-ray or gamma-ray emitting object ABC may be obtained utilizing the principle illustrated in FIG. 1 by the addition of the step of performing a point-by-point inversion of mini-images abc. It is to be noted that a collective inversion of the mini-images abc will not provide an orthoscopic image. It is therefore necessary to make a point-by-point inversion of mini-images abc from the output of detector $D_1$ to obtain the desired orthoscopic image A"B"C" from mini-images a'b'c'. This step may be performed by placing a second, non-inverting, visible-light image intensifier $D_2$ approximately the same distance from the screen S' as the detector $D_1$ is from screen S'. Now, screen S' acts as an inverting screen rather than viewing screen and the mini-images abc from detector $D_1$ are inverted through pinholes $P_1'$ and $P_2'$ into images a'b'c' at the surface of intensifier $D_2$. A third screen S", preferably identical to screen S', may be placed at approximately the same distance from the intensifier $D_2$ as screen S' is to intensifier $D_2$. Screen S" has pinholes $P_1"$ and $P_2"$ therein aligned with pinholes $P_1'$ and $P_2'$ in screen S'. It is to be noted that this pinhole screen analogy relies upon pinhole aperture screen S' to invert mini-images abc rather than to use those mini-images to reconstruct pseudoscopic image A'B'C'. When mini-images a'b'c' are viewed from the right of screen S" through pinholes $P_1"$ and $P_2"$, the rays of mini-images a'b'c' are now divergent in the direction of the viewer. Consequently, a virtual, orthoscopic image A"B"C" of object ABC is formed to the left of screen S". This orthoscopic (true depth) virtual image is situated to the left of the viewing screen S" at approximately the same distance as object ABC is from screen S. Thus, when looking at screen S", the viewer receives a sensation of seeing object ABC through a "window."

Figure 3:
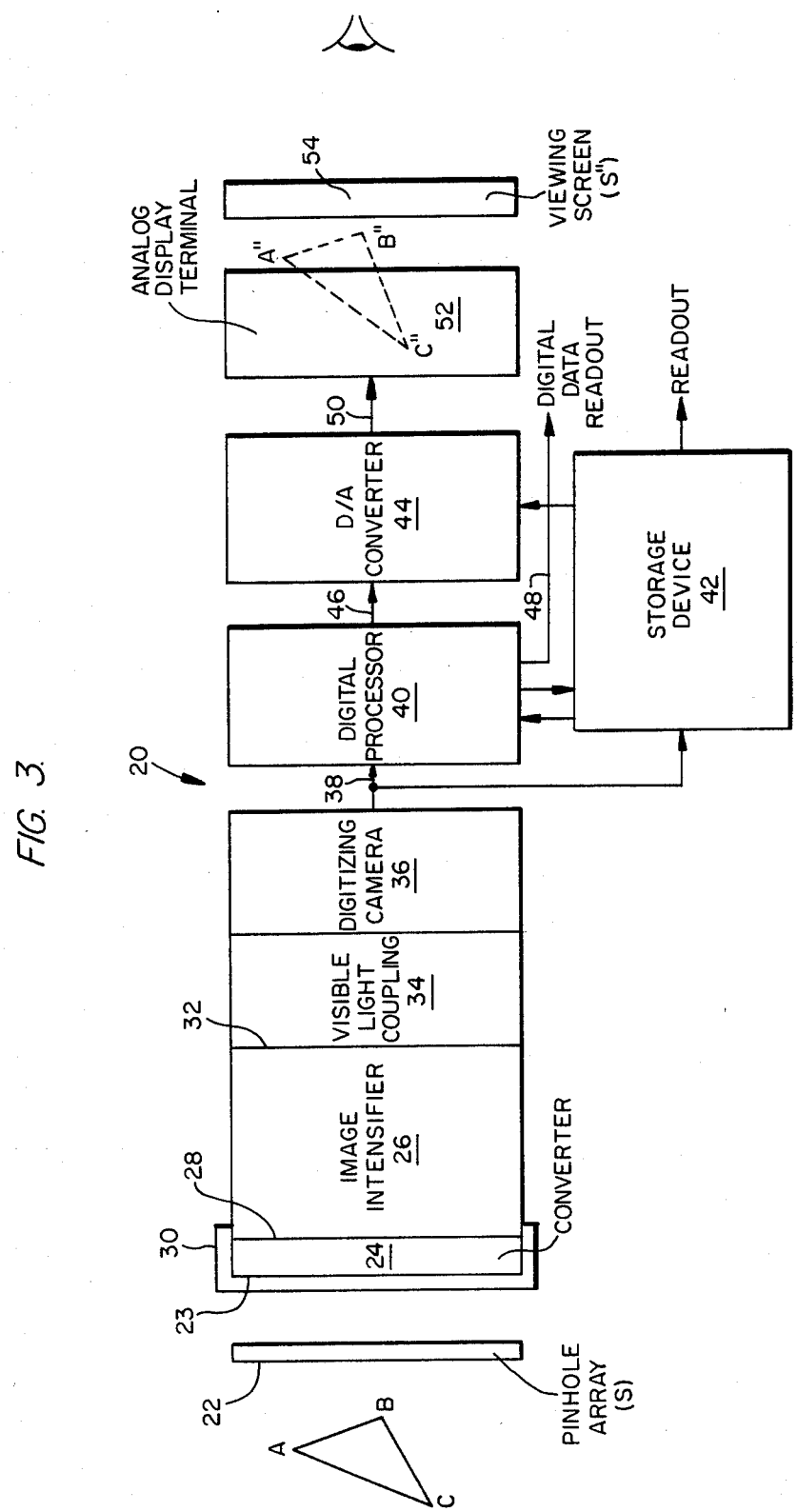
FIG. 3 is a block diagram showing the functional elements of one embodiment of the invention.

FIG. 3 shows the major functional elements of an instrument 20 based on the principles illustrated in FIGS. 1 and 2. A screen 22, made from a thin sheet of a material such as lead, impervious to x-rays and gamma rays and perforated by numerous pinholes of equal area (too small to be shown) and uniformally distributed over the surface of the screen in a predetermined pattern, is placed between object ABC and an x-ray and a gamma-ray converter 24. Each pinhole serves as a separate pinhole camera and produces an inverted mini-x-ray image of the object ABC on converter layer 24. The pinholes are spaced from each other and from the converter 24 so that the mini-images do not significantly overlap each other. Very small pinholes will provide high resolution at the expense of collection efficiency of x and gamma-ray photons. Converter layer 24 is any scintillator material or phosphor, such as a rare-earth phosphor, which serves to convert x-ray and gamma-ray images incident upon it into visible-light images. The visible-light images generated by converter layer 24 are applied directly onto a visible-light image intensifier 26 with its input surface 28 positioned immediately next to converter layer 24. Alternatively, the converter layer 24 may be coupled to the intensifier 26 by an appropriate lens system, not shown, or directly coupled by a fiber optics system, tapered or not tapered, or a combination of a lens system and a fiber optics plate, thus allowing for a converter of a different size than the intensifier input. The converter could be integrated with and located internally within the intensifier 26. Yet another alternative is to locate an x-ray or gamma-ray to electron converter, i.e., a photocathode, within intensifier 26. A thin shield 30, made from a material which is opaque to visible light but transparent to x-rays and gamma rays (e.g., black plastic film), is positioned between screen 22 and converter layer 24 and fitted to cover the entire input surface 23 of converter layer 24 to block visible light from reaching the input surface 28 of the image intensifier 26.

Intensifier 26 intensifies the visible-light output of the converter 24 by a large brightness gain factor of, for example, $10^5$. It can be any device which is linear and provides such a gain without significant spatial distortion of each of the mini-images originally formed on the converter by the pinholes. The intensifier may be either inverting or non-inverting, minifying or 1:1, and may be with or without electron multiplication. Converter 24 and the intensifier 26 essentially function as element $D_1$ shown in FIGS. 1 and 2. In the embodiment of FIG. 3, the output of the intensifier 26 is a visible-light output which is coupled to a digitizing camera 36 by a visible-light coupling 34 which can be a lens system of varying magnification or a fiber optics plate with either a 1:1 magnification or taper, or a combination of a lens system with a fiber optics plate. The digitizing camera 36 must be one which is capable of converting the incident array of mini-images into a digitized format where the digital code represents position, e.g., x and y coordinates, and the corresponding intensity at that position. The resolution of the camera preferably should be sufficient to accurately reproduce the details of the mini-images. Suitable video cameras include those with CCD and CID arrays. Alternatively, if the visible-light output of the image intensifier 26 is replaced by a digital output such as a digitized anode, there will be no need for the visible-light coupling 34 and the digitizing camera 36.

The digitized output 38 of the camera is inputted into both a digital processor 40 and a storage device 42. The processor 40 is programmed to invert each individual mini-image about its respective pinhole, i.e., each image will undergo a 180° rotation about its respective pinhole in order to allow for a later reconstruction of an orthoscopic, three-dimensional image of the x-ray or gamma-ray emitting object. The processor 40, operating as described, functions as elements S' and $D_2$ in FIG. 2 which are shown merely for the purpose of illustration. Data from the digitizing camera 36 would ordinarily be inputted directly into the processor 40 when real-time processing is important or when the processor can run through its programs in essentially real-time. Otherwise, the data from the digitizing camera 36 and the output of the digital processor 40 can be stored in the storage device 42, such as a tape or disk system, for later use, where real-time processing is not essential or possible.

It should be noted that by digitizing the data and employing the processor 40, much more is gained than merely replacing elements $D_1$ and S' as shown in FIG. 2. By having the data in digitized form suitable for computer processing and data storage, it is possible to produce an image of x-ray and gamma-ray objects of extremely low intensity through time integration in order to achieve data with statistical significance. In addition, many algorithms can be utilized to further improve the quality of the reconstructed image, whether digital or analogue. Such algorithms include, for example, smoothing, contrast enhancement, edge enhancement, pseudo-color, background substraction and correction, and the elimination of out-of-focus contributions to tomograms. The digitized data allows for the free adjustment of both the size and the intensity of the mini-images to provide, in the analogue mode, a wide range of magnifications and intensities of the reconstructed three-dimensional x-ray and gamma-ray emitting object for the viewer. Furthermore, because the process of inverting the individual mini-images for orthoscopic reconstruction is accomplished by computation rather than actual optical instrumentation, it is accomplished without concommitant degradation in noise or resolution, thereby preserving the image quality as given by the first imaging detector $D_1$. Because the reconstruction of the x-ray and gamma-ray emitting object in either three-dimensions or tomograms can also be accomplished by computation from the digitized data, quantitative information concerning the object is now available in addition to an orthoscopic visual display. Such quantitative information can be stored permanently and retrieved repeatedly for later investigations. Yet another advantage of the digitized data is the capability of obtaining simultaneous spectral information, i.e., energy distribution, concerning the x-ray and gamma-ray emitting object if the imaging detector output is proportional to the energy of the incident x-rays and gamma rays. Such imaging detectors include, for example, gamma cameras, position-sensitive proportional counters and solid-state detectors, and the modified Lixiscope (low intensity x-ray imaging scope) as disclosed in U.S. Pat. No. 4,345,153. Knowledge of the energy distribution of the incident x-rays and gamma rays not only gives an additional quantitative parameter concerning the object but also allows the application of further enhancement techniques on the reconstructed image. As an example, in nuclear medicine, using the energy information, it is possible to reconstruct the three-dimensional distribution of a radioisotope in an organ, free from Compton-scattered gamma-ray background. Or, if more than one radioisotope is used, one can reconstruct the distribution of each radioisotope free from the interference of the others.

Returning to FIG. 3, the processor 40, having created an individually inverted mini-image array in a digital format, may either be inputted into a digital-to-analogue (D/A) converter 44 via line 46 for later optical analogue three-dimensional reconstruction, or it may reconstruct three-dimensional and tomographic images in digital form by computation for direct readout on digital data readout line 48 or storage in device 42 for later use. The D/A converter 44 merely represents a functional block of the system and does not necessarily represent a physical unit. It may be a physical unit, or, alternatively, be part of either the processor 40 output or part of the analogue display terminal 52.

The essential function performed by the D/A converter 44 is to convert the digitized, individually inverted mini-images into analogue signals which can be processed into visible form suitable for optical reconstruction, e.g., the analogue form can be a transparency formed from, for example, photographic film showing the array of mini-images with an appropriate grey-scale corresponding to the intensity level of the output of the intensifier 26. Alternatively, the analogue signals may be coupled at line 50 to drive an analogue video display terminal 52 which may be a conventional cathode-ray tube or television type monitor.

In the event that a transparency is developed, the transparency, which will contain a multiplicity of mini-images, should be first illuminated with diffused light and the single three-dimensional image A"B"C" can then be reconstructed with the viewing screen 54 which corresponds to S" on FIG. 2. If a video display monitor is employed, again there is a display of a multiplicity of mini-images which are already light-emitting and can, thereafter, be viewed through the viewing screen 54 to reconstruct a three-dimensional image. The reconstructed image will be orthoscopic. The viewing screen 54 may be spaced from the illuminated transparency or display 52 at a distance which is approximately the same distance as pinole array 22 is spaced from the input surface 23 of the converter 24. The viewing screen 54 can be an array of pinholes with an arrangement similar to that of pinhole array 22 but the material from which it is constructed need not be that which blocks x and gamma rays, i.e., it need only block visible light. As an example, an appropriate transparency (not shown) may be used without any physical holes but, rather, the transparent portions would relate to the pinhole positions. The pinhole size of the viewing screen 54 should be large enough to avoid diffraction of visible light but small enough to allow for adequate resolution of the details of the mini-images. It should be noted that diffraction is not a consideration for pinhole array 22 because of the extremely short wavelengths of x-rays and gamma rays with respect to the pinhole diameters. While the pinhole patterns should be identical with the pattern of pinhole array 22, the dimensions of the pattern need not be identical so that any minification or magnification of the mini-images provided by the display 52 or the transparencies, for instance, can be accommodated for reconstruction of a minified or magnified three-dimensional orthoscopic image of the x-ray or gamma-ray emitting object. The depth of the reconstructed image can be exaggerated without affecting its lateral dimensions by increasing the viewing screen 54 to analogue display 52 separation distance.

If a proportional reconstruction is desired, all dimensions concerning the mini-images as well as the viewing screen must be adjusted accordingly. Because the display 52 or an illuminated transparency give the mini-images in a visible format, a properly designed fly's-eye lens, having the same pattern as the pinhole array, may be substituted for the viewing screen 54, thus greatly increasing both the brightness of the reconstructed image as well as the resolution. Due to the short focal length of the fly's-eye lens, the fly's-eye viewing screen can be in close proximity to or placed in direct contact with, the mini-images. The fly's-eye viewing screen has the further advantages of providing adequate viewing under normal ambient light conditions as well as more comfortable viewing.

It should be emphasized that the availability of both quantitative digital data and three-dimensional analogue viewing has a distinct advantage because when the viewer has once seen the three-dimensional, orthoscopic display of the object, subsequent interpretation and analyses of, for instance, tomograms, developed from the digital information, becomes immeasurably easier. If the x-ray or gamma-ray emitting object is substantially stationary, the field of view of the described device can be substantially increased by sequentially moving the detector portion of the device, i.e., the elements of the device, 23 through 36, in a predetermined scanning fashion behind a substantially larger pinhole array 22. The mosaic of the mini-image arrays thus obtained must be processed accordingly to obtain analogue and digital reconstructions of the emitting object.

It should also be emphasized that with reference to FIG. 3, a photographic film can be substituted for the image intensifier 26 or it can be placed at the output of the image intensifier. Alternatively, an x-ray film can be used directly behind the pinhole array 22 as the imaging detector. A densitometer can be used to digitize the information on the developed photographic or x-ray film prior to feeding the information into the digital processor 40 or storage device 42. Similarly, any position-sensitive x-ray and gamma-ray detector with a direct or converted digital output can be used in lieu of elements 23 through 36. Some typical position-sensitive x-ray and gamma-ray detectors include multi-wire gas proportional counters, solid-state imaging detectors, scintillation crystal or photomultiplier combinations with centroiding electronics such as those used in present-day gamma cameras, and the modified Lixiscope.

Whereas the invention has been shown and described with respect to the preferred embodiment, it should be understood that modification may be made and equivalents substituted therefor without departing from the spirit and scope of the invention. Accordingly, all modifications, changes and alterations coming within the spirit and scope of the invention, as defined in the appended claims, are herein meant to be included.

What is claimed is:

1. An instrument for obtaining quantitative, three-dimensional and tomographic information relating to x-ray and gamma-ray emitting objects, and for the orthoscopic viewing of such objects, comprising:
   means for forming incident x-rays and gamma-rays emitted by an object into an array of substantially nonoverlapping mini-images of said object;

means spatially displaced from said forming means for converting said x-ray and gamma-ray mini-images into visible-light mini-images;

means coupled to said converting means for intensifying said visible-light mini-images;

means to digitize said intensified visible-light mini-images;

computing means for processing said digitized mini-images for tomographic and three-dimensional reconstruction of said object; and viewing means for direct orthoscopic, three-dimensional viewing of the reconstructed x-ray and gamma-ray emitting object.

2. The instrument of claim 1 wherein said forming means is a pinhole array.

3. The instrument of claim 2 wherein said pinhole array is formed from material which is impervious to x-rays and gamma rays.

4. The instrument of claim 2 wherein the diameter of the pinholes of said pinhole array is sufficiently large for adequate collection efficiency while being sufficiently small for adequate resolution.

5. The instrument of claim 2 wherein said pinhole array is formed in a predetermined pattern.

6. The instrument of claim 5 wherein said predetermined pattern does not produce substantially overlapping mini-images of said objects on said converting means.

7. The instrument of claim 1 wherein said converting means is any scintillation or phosphor material capable of converting x-rays and gamma rays into visible light.

8. The instrument of claim 1 wherein said converting means is directly coupled to said intensifying means.

9. The instrument of claim 8 wherein said direct coupling is through a fiber optics plate.

10. The instrument of claim 9 wherein said fiber optics plate is tapered.

11. The instrument of claim 1 wherein said converting means is coupled to said intensifying means through a lens system.

12. The instrument of claim 1 wherein said converting means is located within said intensifying means.

13. The instrument of claim 1 wherein said intensifying means is a visible-light intensifier with a visible-light output.

14. The instrument of claim 1 wherein said intensifying means includes electron multiplication means.

15. The instrument of claim 1 wherein said intensifying means does not include electron multiplication means.

16. The instrument of claim 14 wherein said electron multiplication means includes at least one micro-channel plate multiplier.

17. The instrument of claim 1 wherein said intensifying means includes an output image size of substantially the same size as the array of mini-images impinging on the input of said intensifying means.

18. The instrument of claim 1 wherein said intensifying means outputs an image size different from that of the array of mini-images impinging on the input of said intensifying means.

19. The instrument of claim 18 wherein said output image size is less than said array of input mini-images.

20. The instrument of claim 18 wherein said output image size is greater than said array of input mini-images.

21. The instrument of claim 1 wherein said digitizing means is a digitizing anode of said intensifying means.

22. The instrument of claim 1 wherein said digitizing means converts the output of said intensifying means to digital words relating to the position and intensity of said mini-images.

23. The instrument of claim 1 wherein said digitizing means is a visible-light digitizing videocamera optically coupled to said intensifying means and wherein said intensifying means provides a visible-light output.

24. The instrument of claim 23 wherein said optical coupling is through a fiber optics plate.

25. The instrument of claim 24 wherein said fiber optics plate is tapered.

26. The instrument of claim 23 wherein said optical coupling is through a lens system.

27. The instrument of claim 23 wherein said digitizing camera is directly coupled to said intensifying means.

28. The instrument of claim 2 wherein said computing means processes said digitized mini-images by inverting said digitized images about their respective pinhole position.

29. The instrument of claim 2 wherein said computing means reconstructs said object through back-projection of said mini-images through their respective pinholes by computation techniques.

30. The instrument of claim 1 wherein said computing means develops tomograms of said object from said mini-images through computation techniques.

31. The instrument of claim 8 wherein said coupling is a lens system combined with a fiber optics plate.

32. The instrument of claim 1 wherein said intensifying means provides an output which inverts said array of mini-images appearing at its input.

33. The instrument of claim 1 wherein said intensifying means provides an output which is proportional to the energy of the x-rays and gamma rays emitted by said object.

34. The instrument of claim 33 wherein said digitizing means converts the output of said intensifying means to digital words relating to said energy of said x-rays and gamma-rays in addition to the position and intensity of said mini-images.

35. The instrument of claim 1 wherein said intensifying means is coupled to said digitizing means by a combination of a lens system and a fiber optics plate.

36. The instrument of claim 1 wherein said computing means includes storage means.

37. The instrument of claim 36 wherein said storage means includes a magnetic medium.

38. The instrument of claim 28 wherein said inverted mini-images are converted to analogue signals.

39. The instrument of claim 38 wherein said analogue signals are processed into a transparency with an appropriate grey-scale corresponding to said signals, said transparency being part of said viewing means.

40. The instrument of claim 38 wherein said analogue signals are processed into a false color transparency where the colors correspond to the energies of said x-rays and gamma rays of said emitting objects, said transparency being part of said viewing means.

41. The instrument of claim 38 wherein said analogue signals are employed to drive a television type display with an appropriate grey-scale corresponding to said signals, said display being part of said viewing means.

42. The instrument of claim 41 wherein said display is a color terminal with its color corresponding to the energies of the x-rays and gamma-rays emitted by said object.

43. The instrument of claim 2 wherein said viewing means includes both an analogue display and a pinhole array with substantially the same pattern as said forming means, said pinhole array being displaced from said analogue display.

44. The instrument of claim 5 wherein said viewing means includes both an analogue display and a fly's-eye lens with substantially the same pattern as said forming means.

45. The instrument of claim 43 wherein the dimensions of said pinhole array are dependent on the dimensions of said mini-images as shown on said analogue display.

46. The instrument of claim 44 wherein the dimensions of said fly's-eye lens are dependent on the dimensions of said mini-images as shown on said analogue display.

47. An instrument for obtaining quantitative, three-dimensional and tomographic information of x-ray and gamma-ray emitting objects, and for orthoscopic viewing of such objects, comprising:
means for forming incident x-rays and gamma rays emitted by an object into an array of substantially non-overlapping mini-images of said object;
means spatially displaced from said forming means for the detection of said x-rays and gamma-ray mini-images;
means to digitize said detected mini-images;
computing means for processing said digitized mini-images for tomographic and three-dimensional reconstruction of said object; and
viewing means for direct orthoscopic, three-dimensional viewing of the reconstructed x-ray and gamma-ray emitting object.

48. The instrument of claim 47 wherein said forming means is a pinhole array.

49. The instrument of claim 47 wherein said detection means includes an x-ray film.

50. The instrument of claim 47 wherein said detection means includes an intensifier for x-rays or gamma rays.

51. The instrument of claim 47 wherein said detection means includes a position sensitive gas proportional counter.

52. The instrument of claim 47 wherein said detection means includes a position sensitive, solid-state detector.

53. The instrument of claim 47 wherein said digitizing means includes means to indicate the position and intensity of said mini-images.

54. The instrument of claim 53 wherein said digitizing means includes means to indicate the energy of said mini-images.

55. The instrument of claim 47 wherein said computing means includes means for positional inversion of said individual mini-images.

56. The instrument of claim 47 wherein said computing means includes means for back-projection calculations of said mini-images for the reconstruction of said x-ray and gamma-ray emitting object.

57. The instrument of claim 47 wherein said computing means includes means for the development of tomograms of said x-ray and gamma-ray emitting object.

58. The instrument of claim 47 wherein said viewing means includes a transparency of said mini-images with a viewing screen with the same pattern as said array.

59. The instrument of claim 47 wherein said viewing means includes a video monitor with a viewing screen with the same pattern as said array.

60. The instrument of claim 47 wherein said detection means includes any x-ray or gamma-ray to visible-light converter in combination with photographic film.

61. The instrument of claim 47 wherein said detection means includes an x-ray and gamma-ray intensifier in combination with photographic film.

62. An instrument for obtaining quantitative, three-dimensional and tomographic information of x-ray and gamma-ray emitting objects, and for orthoscopic viewing of such objects, comprising:
means for forming incident x-rays and gamma rays emitted by an object into an array of substantially non-overlapping mini-images of said object;
means spatially displaced from said forming means for the detection of said x-ray and gamma-ray mini-images;
means to digitize said detected mini-images; and
computing means for processing said digitized mini-images for tomographic and three-dimensional reconstruction of said object.

* * * * *